(12) United States Patent
Jackson

(10) Patent No.: US 6,368,321 B1
(45) Date of Patent: Apr. 9, 2002

(54) LOCKABLE SWIVEL HEAD BONE SCREW

(76) Inventor: Roger P. Jackson, 66 Indian La., Mission Hills, KS (US) 66208

( * ) Notice: Subject to any disclaimer, the term of this patent is extended or adjusted under 35 U.S.C. 154(b) by 0 days.

(21) Appl. No.: 09/729,399

(22) Filed: Dec. 4, 2000

(51) Int. Cl.$^7$ ............................................. A61B 17/70
(52) U.S. Cl. ........................................................ 606/61
(58) Field of Search ............................ 606/61, 60, 72, 606/73

(56) References Cited

U.S. PATENT DOCUMENTS

| | | | |
|---|---|---|---|
| 5,312,404 A | | 5/1994 | Asher et al. |
| 5,429,639 A | * | 7/1995 | Judet ............................ 606/61 |
| 5,443,467 A | | 8/1995 | Biedermann et al. |
| 5,476,464 A | | 12/1995 | Metz-Stevenhagen et al. |
| 5,601,553 A | | 2/1997 | Trebing et al. |
| 5,669,911 A | | 9/1997 | Errico et al. |
| 5,672,176 A | * | 9/1997 | Biedermann et al. .......... 606/61 |
| 5,817,094 A | * | 10/1998 | Errico et al. .................... 606/61 |
| 5,879,350 A | | 3/1999 | Sherman et al. |
| 6,063,090 A | | 5/2000 | Schlapfer |
| 6,074,391 A | | 6/2000 | Metz-Stavenhagen et al. |
| 6,077,262 A | | 6/2000 | Schlapfer et al. |
| 6,090,111 A | * | 7/2000 | Nichols ........................ 606/61 |
| 6,132,432 A | * | 10/2000 | Richelsoph .................... 606/61 |
| 6,146,383 A | * | 11/2000 | Studer et al. ................... 606/61 |
| 6,224,596 B1 | * | 5/2001 | Jackson ........................ 606/61 |
| 6,254,602 B1 | * | 7/2001 | Justis ............................ 606/61 |
| 6,273,888 B1 | * | 8/2001 | Justis ............................ 606/61 |
| 6,280,442 B1 | * | 8/2001 | Barker et al. .................. 606/60 |
| 6,287,311 B1 | * | 9/2001 | Sherman et al. ............... 606/78 |
| 6,302,888 B1 | * | 10/2001 | Mellinger et al. ............. 606/73 |
| 2001/0001119 A1 | * | 5/2001 | Lombardo .................... 606/73 |

FOREIGN PATENT DOCUMENTS

| | | | |
|---|---|---|---|
| DE | 92 02 745 8 | | 4/1992 |
| DE | 195 07 141 A 1 | | 9/1996 |

OTHER PUBLICATIONS

*EBI Omega 21* Brochure, EBI Spine Systems, pub. 1999.
*Claris Instrumentation* Brochure, G Med, pub. 1997.
*VLS System Variable Locking Screw* Brochure, Interpore Cross International, pub. 1999.
*CD Horizon M8 Multi Axial Screw Spinal System* Brochure, Medtronic Sofamore Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct., 1999.
*Silhouette Spinal Fixation System* Brochure, Sulzer Medica Spine–Tech, no publish date.
*SDRS Surgical Dynamics Rod System* Brochure, Surgical Dynamics, pub. 1998–99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

* cited by examiner

Primary Examiner—Eduardo C. Robert
(74) Attorney, Agent, or Firm—John C. McMahon

(57) ABSTRACT

A bone screw having a head and a shank. The shank having a ball thereon and the head having a socket for receiving the ball. The ball being externally threaded and the chamber communicating with the exterior of the head through a threaded bore. The ball being threadably received through the bore and being swivable in the chamber after passing through the bore. The bone screw including at least one set screw that operably engages the ball to lock the head in position relative to the shank.

17 Claims, 2 Drawing Sheets

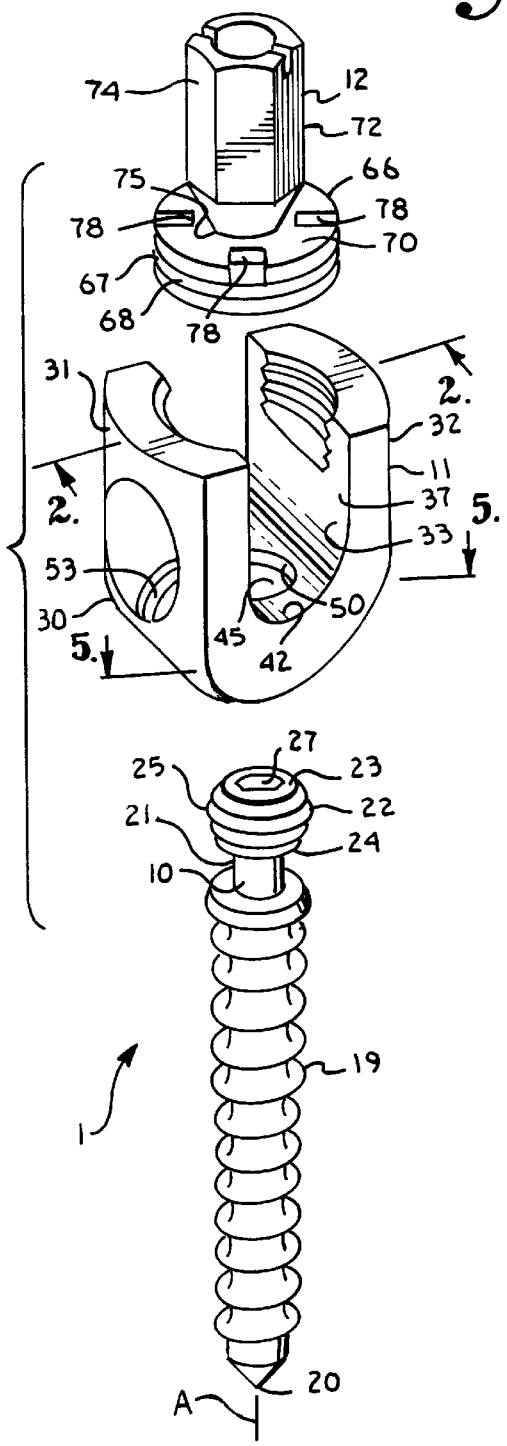
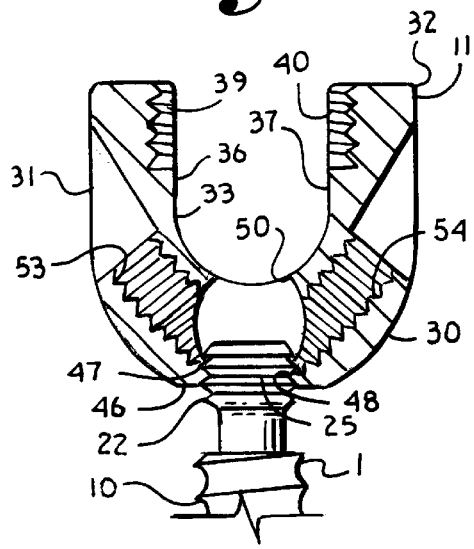

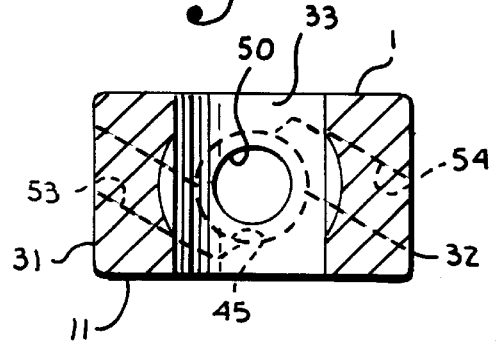
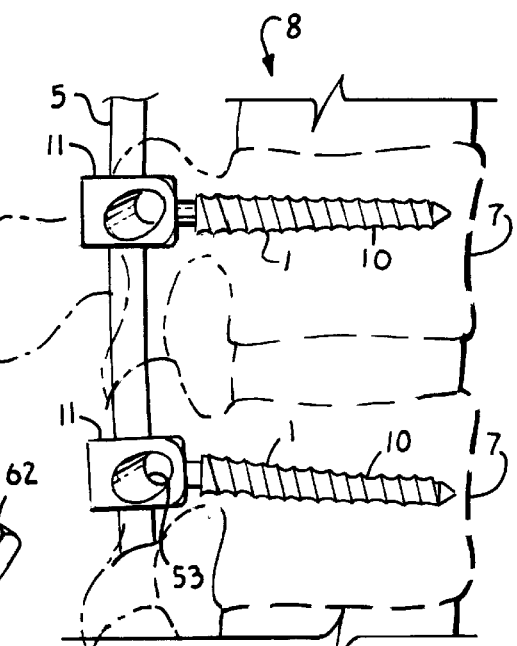
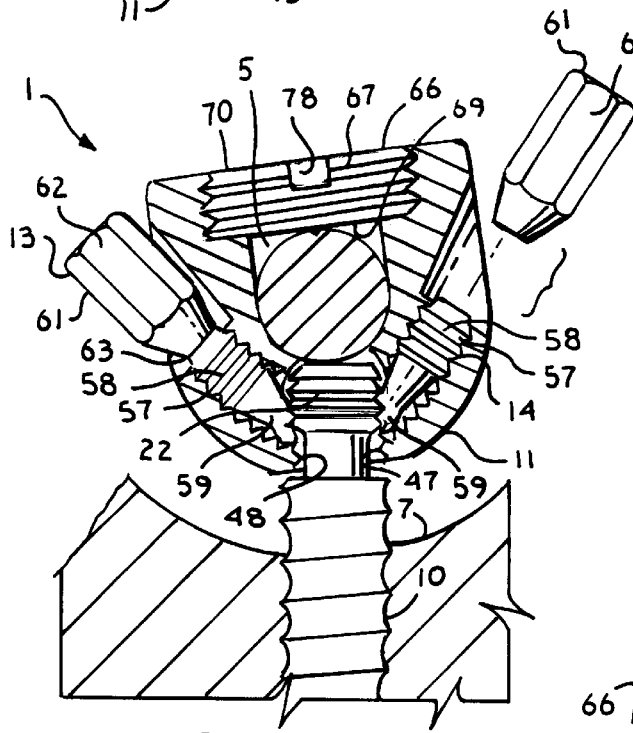
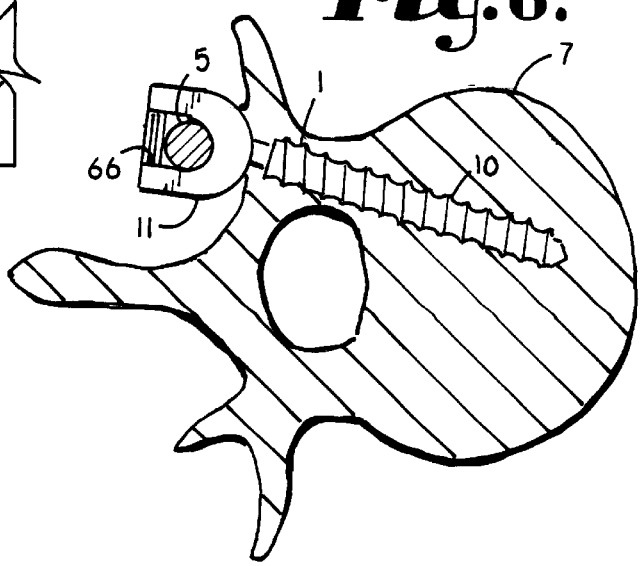

LOCKABLE SWIVEL HEAD BONE SCREW

BACKGROUND OF THE INVENTION

The present invention is directed to a bone screw of the type wherein a head of the bone screw is swingable or can swivel about the shank of the bone screw until the surgeon is satisfied with the relative placement of the two parts and thereafter the head can be locked in position relative to the shank.

Bone screws are utilized in many types of spinal surgery in order to secure various implants to vertebrae along the spinal column. Bone screws of this type typically have a shank that is threaded and adapted to be implanted into a vertebral body of a vertebrae. The bone screw also includes a head which is designed to extend beyond the vertebrae and which has a channel to receive another implant. Typically the channel will receive a rod or a rod-like member. In bone screws of this type, the head may be open, in which case a closure must be used to close between opposite sides of the head once a rod-like implant is placed therein, or closed wherein a rod-like implant is threaded through the head of a bone screw.

When the head and shank of the bone screw are fixed in position relative to each other, it is not always possible to insert a bone screw in such a manner that the head will be in the best position for receiving other implants. Consequently, swivel head bone screws have been designed that allow the head of the bone screw to rotate or swivel about an upper end of the shank of the bone screw while the surgeon is positioning other implants and finding the best position for the bone screw head. However, once the surgeon has determined that the head is in the best position, it is then necessary to lock or fix the head relative to the shank and different types of structures have been previously developed for this purpose. Unfortunately, the prior art devices have a tendency to be bulky, slip under high loading or require many parts.

It is desirable to have a swivel head bone screw that can be captured by the shank prior to locking of the head, but that allows the head to freely swivel or pivot about a top of the shank prior to locking. It is then further desirable to have the head that can be fixably locked in a configuration or position relative to the shank where the head best fits with other elements of the overall spinal implant.

Furthermore, it is desirable to maintain the number of parts of the device at a minimum. Also, it is desirable to secure the various parts together in such a way, so that, if parts become loose under use for some reason, the device will not totally disassemble.

SUMMARY OF THE INVENTION

A bone screw for use in conjunction with spinal surgery and, in particular, for implanting into a bone and securing other medical implants to the bone. The bone screw includes a head and a shank.

The shank has a lower portion which is threaded and sized and shaped to be operably screwed into a vertebral body in the spine of a patient. The end of the shank opposite the threaded lower portion includes a ball having a partial external thread thereon that is coaxial with an axis of rotation of the shank. The top of the shank includes a bore, preferably having a hexagonal cross-section or the like that is adaptable to a tool such as an alien wrench for driving the shank into the bone.

The head of the bone screw may be either an open or a closed type. Both types have a central channel that passes at least partially through the head. In the open type, the channel is open all the way to the top of the head and is closed after the placement of another implant into the channel by a closure. Where the head is closed, the channel that receives the implant is open on both ends, but encircled by the head.

The base of the head includes a chamber which is sized and shaped to fairly snugly receive the ball of the shank. In this manner the chamber and top of the shank function as a ball and socket arrangement that allows swiveling of the head relative to the shank until the head is locked relative to the shank. The chamber is connected to an exterior of the head by a threaded bore that is sized and shaped to threadably receive the ball from the shank with a minimum number of full rotations of the thread. That is, there are relatively few full 360° turns of the thread on the ball such that the ball very quickly can be screwed through the bore and into the chamber. Once within the chamber, the thread on the ball becomes disengaged from the thread on the bore and the ball is able to freely rotate within the chamber, until locked.

At least one additional bore extends from an exterior of the head so as to intersect with the chamber. The second bore is aligned to intersect with the ball and receives a first set screw, when the ball is in the chamber or socket, that preferably engages the ball somewhat tangentially or at an offset angle with respect to the radius of the ball. The first set screw is also designed to engage the thread on the ball and to urge the ball against the sidewall of the chamber so as to lock the ball in position relative to the head. This in turn locks the shank in a fixed position or configuration relative to the head.

Preferably, a third bore and second set screw are located opposite the second bore and first set screw and the second set screw also operably engages the ball in a non-radial manner so as to likewise urge the ball against the wall of the chamber and to fix the ball in position relative to the head. Each set screw also preferably includes a tip which is partially deformable upon engaging the ball so as to help secure the ball in position and to enlarge and resist inappropriate disengagement of the set screw from the bore within which it is received. Also, each of the set screws preferably includes a breakaway installation head that is designed to break off at a preselected torque so as to set the set screws at a desired uniform torque with each installation.

OBJECTS AND ADVANTAGES OF THE INVENTION

Therefore, the objects of the present are: to provide a bone screw for implantation into a vertebra of a patient wherein the head of the bone screw is swingable or swivable about an end of a shank of the bone screw until a desired configuration is obtained after which the head is lockable in position relative to the shank; to provide such a bone screw wherein the shank includes a ball at one end thereof that is captured by the head, yet allows the head to remain swivable after capture; to provide such a bone screw wherein the shank ball is threaded exteriorly and wherein the head includes a chamber that is spaced from the exterior by a threaded bore that threadably receives the head and allows the head to pass from the exterior by screwing into the chamber after which the threads of the ball and bore disengage so that the ball is free to rotate and swing about within the chamber; to provide such a bone screw wherein a second bore is provided that extends from the exterior of the head to intersect with the chamber and receive a set screw therein that abuts against the ball when the set screw is advanced within the second bore; to provide such a set screw wherein the set screw engages the thread of the ball in a non-radial and somewhat tangential manner so as to urge the ball against the sidewall of the chamber and to lock the ball in position so that the shank is in turn locked in position relative to the head; to provide such a bone screw wherein the set screw includes a tip that expands upon engaging the ball to better resist relative movement of the ball and to also resist unplanned withdrawal of the set screw from the second bore due to vibration or the like; to provide such a bone screw swivel head which is readily adaptable for both open-headed and closed-headed bone screws; to provide such a bone screw wherein a single size head may be utilized in conjunction with various shank lengths such that fewer sizes of comparatively expensive bone screw heads are necessary to be kept in inventory; and to provide such a bone screw which is relatively easy to use and especially well suited for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a bone screw in accordance with the present invention having a shank, a head and a closure therefor.

FIG. 2 is an enlarged and fragmentary cross-sectional view of the screw, taken along line 2—2 of FIG. 1, illustrating a step in the joining of the head to the shank.

FIG. 3 is an enlarged and fragmentary cross-sectional view of the bone screw, similar to FIG. 2, showing a ball of the shank being captured in a socket of the head.

FIG. 4 is a fragmentary and enlarged partial cross-sectional view of the bone screw shown in a vertebrae, similar to FIG. 2, with a rod captured in a channel of the head and by the closure and with a pair of set screws with breakaway heads being positioned to lock the shank relative to the head with one of the set screw heads shown as having broken away.

FIG. 5 is an enlarged and cross-sectional view of the bone screw, taken along line 5—5 of FIG. 1.

FIG. 6 is a top plan view of the bone screw located in a vertebra that is shown in cross section with the head of the bone screw receiving the rod and being locked in position relative to the shank.

FIG. 7 is a side elevational view of a pair of bone screws supporting a rod and positioned in vertebrae which are illustrated in the phantom.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a bone screw in accordance with the present invention. The bone screw 1 captures a rod 5 and is implanted in a vertebra 7 of a patient's spine 8. The bone screw 1 includes a shank 10, a head 11, a closure 12 for the head and a pair of locking set screws 13 and 14.

The shank 10 is sized and shaped to be screwed into one of the vertebrae 7. The shank 10 includes an external thread 19 that extends from an outward tip 20 to near a top 21 thereof. The top 21 includes an upper portion or ball shaped structure 22 that is truncated on a top 23 and bottom 24 thereof and has an external thread 25. The ball shaped structure 22 has an external surface that is curved in vertical cross-section in the region of the thread 25, whereas the thread 25 is cut on a cylindrical basis such that a depth associated with the thread 25 varies significantly vertically over the structure 22. In particular, the thread 25 is deepest and extends out the furthest at the most laterally extending portions of the ball shaped structure 22 from an axis of rotation A of the shank 10.

A bore 27 extends coaxially inward from the top of the ball shaped structure 22 and has a generally hexagonal cross-section in a plane perpendicular to the axis of rotation A of the shank 10. The bore 27 is sized and shaped to receive a conventional installation tool (not shown), such as an allen wrench or the like for driving the shank 10 into the vertebra 7.

The head 11 is generally U-shaped having a body 30 with a pair of spaced but generally parallel arms 31 and 32 that form a channel 33 therebetween. Inside facing surfaces 36 and 37 of arms 31 and 32 respectively are threaded with discontinuous, but helically wound thread portions 39 and 40 respectively. The channel 33 has a lower seat 42 which is designed and shaped to snugly receive the rod 5 during use.

The head body 30 includes a chamber 45. The chamber 45 is sized and shaped to fairly snugly, but slidingly, receive the shank ball shaped structure 22 therein. The chamber 45 communicates with and opens onto a body lower end 46 through a bore 47 that is generally circular in cross-section and includes an internal thread 48. The thread 48 is sized and shaped to matingly receive the ball shaped structure thread 25 as the shank 10 is rotated. In this manner the ball shaped structure 22 is threadedly received through the bore 47 by rotation of the shank 10 until it passes through the bore 47 and into the chamber 45 upon which occurrence the threads 25 and 48 disengage. In this manner the outwardly extending thread 48 prevents the ball shaped structure 22 from being pulled from the chamber 45, unless it is unscrewed therefrom again through the bore 47, but allows the ball shaped structure 22 to freely rotate in the chamber 45 until locked in place as described below. In this manner the head 11 is able to swivel or swing about the upper end or top 21 of the shank 10 until subsequently locked in place.

An upper end of the chamber 45 also communicates with and opens into the channel 33 through an aperture 50. The aperture 50 is positioned to be above the ball shaped structure 22 and especially the hex bore 27 when the ball shaped structure 22 is in the chamber 45 to allow access of a tool to the bore 27 for purposes of removal of the bone screw 1 from the vertebra 7.

The head 11 also includes a pair of threaded bores 53 and 54 which extend inward from opposite outer surfaces of the arms 31 and 32 and intersect with the chamber 45 on opposite sides thereof respectively. The bores 53 and 54 are preferably at substantial angles with respect to the horizontal, such as is seen in FIGS. 3 and 4 and also are angled to intersect with the chamber 45 so as to intersect with the ball shaped structure 22 slightly inward from a tangent thereof, when the ball shaped structure 22 is in the chamber 45, as is seen in FIG. 5.

Threadably mounted in the bores 43 and 44 are the set screws 13 and 14 respectively, as is seen in FIG. 4. Each 19 of the set screws 13 and 14 have a body 57 with an outer threaded surface 58 and a tip 59. The tip 59 is elongate and generally triangular or trapezoidal in shape with a blunted or rounded distal surface. The tip 59 is designed to somewhat deform upon compression as will be discussed below.

Each of the set screws 13 and 14 also include a head 61 having an outer multifaceted surface 62 that is sized and shaped to receive a conventional socket type tool (not shown) for driving and rotating the head 61. The head 61 is connected to the body 57 by a breakaway region 63. As can be seen in FIG. 4, the set screw 14 on the right hand side has been torqued to a preselected torque and the head 61 has broken from the body 57, leaving the body 57 in place in the bore 54. Although a pair of set screws 13 and 14 are illustrated as being used herein with the present invention, it is foreseen that only a single set screw or alternatively a large number of set screws of the type of 13 and 14 could be utilized in conjunction with the invention.

The closure 12 has a generally cylindrically shaped body 66 with a radially outward threaded surface 67. A thread 68 on the surface 67 is designed to matingly engage the thread portions 39 and 40 on the arms 31 and 32 respectively. The body also includes a lower surface 69 and an upper surface 70. The lower surface 69 operably engages the rod 5 when the closure 12 is screwed between the arms 31 and 32.

The body 66 also originally is secured to an installation or driving head 73, seen in FIG. 1. The driving head 73 has a multifaceted polyhedral cross-sectioned outer surface 74 that is sized and shaped to receive a conventional socket type driving tool (not shown) during installation of the closure 12 into the head 11. The driving head 73 is secured to the body 66 by a breakaway region 75, such that the driving head 73 breaks from the body 66 when a preselected torque is applied to the closure head 73 and only the body 66 remains in the bone screw head 11 thereafter, as is seen in FIG. 4. The body 66 also includes four slots 78 that extend radially inward from the outer surface 58 and intersect with the upper surface 70. The slots 78 are mateable with a tool (not shown) subsequent to installation of the closure 12 in the head 11 to allow counter-rotation of the closure 12 for purposes of removal, should such be necessary.

While a head 11 of the type that is generally referred to as an open headed bone screw head and that requires the closure 12 is illustrated herein, it is also seen that bone screw heads of the closed type may also be utilized in conjunction with the invention. A closed headed bone screw utilizes a channel that opens on two opposite sides of the head and does not open outwardly at the top, so that the head encircles a rod. That is, the head would be circular or oval shaped, as opposed to being U-shaped as in the illustrated embodiment. In such situations the rod 5 must be threaded through the channel in the closed head. Normally, a closed head would also incorporate a set screw that would come inwardly from the top and engage the rod 5, so as to lock the rod 5 in place relative to the head.

Further, although a closure 12 of a particular type is shown herein, it is foreseen that various types of closures such as closures having retained heads for driving or removal may be utilized in conjunction with the invention.

The closure 12 can also include a central bore that may be utilized for both attachment of a tool to be used during installation and/or for insertion of a set screw that is sized and shaped to abut against the rod 5 during use for locking the rod 5 in position relative to the head 11.

In use the shank 10 is initially screwed into a vertebra 7. The head 11 is then positioned such as is shown in FIG. 2 and rotated so that the ball shaped structure thread 25 engages and mates with the bore thread 48 to allow the ball shaped structure 22 to pass through the bore 47, as is seen in FIG. 3. In FIG. 3 the threads 25 and 48 have disengaged and the ball shaped structure 22 is free to rotate or swivel relative to the chamber 45 so that the head 11 can swing or swivel on the top end of the shank 10.

Once the surgeon has aligned and positioned the head 11 relative to the shank 10, normally by insertion of a rod 5 and closure 12 for capturing the rod 5, the set screws 13 and 14 are inserted in the bores 53 and 54 and torqued until the set screw heads 73 break therefrom. The set screw tips 59 are in this manner driven into the ball shaped structure 22, such as is shown in FIG. 4. The tips 59 preferably somewhat deform as they engage the ball shaped structure 22 so as to resist against inadvertent removal of the set screws 13 and 14 from their respective bores 53 and 54 and to very tightly engage the ball shaped structure 22. Preferably the tips 59 engage the ball shaped structure in the region of the thread 25 so as to use the thread 25 to help lock the shank 10 in position relative to the head 11. Preferably, the ball shaped structure 22 is urged by the set screws 13 and 14 into tight engagement with the chamber 45 and/or locked between the set screws 13 and 14 themselves so as to lock the ball shaped structure 22 against swiveling, swinging or rotation relative to the head 11. Before or after the head 12 is locked in place and after the surgeon is satisfied with the position of the rod 5, the closure 12 is tightened by rotation thereof through the closure driving head 73 until the driving head 73 breaks away from the body 66 at a preselected torque (see FIG. 4 which shows the body 66 without the driving head 73).

If it is necessary for some reason to remove part or all of the bone screw 1, the closure 12 may be removed by use of a projecting pin tool mating with and received in the slots 78 to allow counterclockwise rotation of the closure 12. Once the closure body 66 is removed, the rod 5 may be removed or readjusted. If it is necessary the bone screw may then also be removed by use of an allen-type wrench inserted in the shank bore 27 that is exposed through the aperture 50 and the channel 33 and which is rotated counterclockwise to remove the shank 10 from the vertebra 7.

It is to be understood that while certain forms of the present invention have been illustrated and described herein, it is not to be limited to the specific forms or arrangement of parts described and shown.

What is claimed and desired to be secured by Letters Patent is as follows:

1. A swivel head bone screw for surgical implantation; said screw composing:

a) a shank having an axis of rotation with a lower threaded portion coaxial with said axis and adapted for implantation into a vertebra; said shank having an upper portion opposite said lower threaded portion; said upper potion having a second thread located thereon;

b) a head having a channel adapted to receive a rod member therein; said head including a lower chamber sized and shaped to receive said shank upper portion;

c) said head having a threaded first bore communicating between said chamber and an exterior of said head; said bore being sized, shaped and threaded so as to threadably receive said shank upper portion therethrough; said shank upper portion operably passing through said bore and into said chamber during installation and said shank upper portion being swivelable relative to said head when fully in said chamber to allow said head to be captured by but swivelable relative to said shank;

d) said head having a threaded second bore intersecting with said chamber; and e) a threaded set screw operably threadedly received in said second bore and being urgeable against said shank upper portion when said shank upper portion is located in said chamber in order to lock said upper portion in position relative to said head.

2. The screw according to claim 1 wherein:

a) said first bore is located on a side of said chamber opposite said channel.

3. The screw according to claim 1 wherein:

a) said head is generally U-shaped.

4. The screw according to claim 3 including:

a) a closure plug having a threaded outer surface and wherein:

b) a said head includes a pair of spaced arms having facing threads sized and shaped to threadably receive said plug.

5. The screw according to claim 1 wherein:

a) said shank upper portion is generally spherical in shape.

6. The screw according to claim 5 wherein:

a) said chamber is sized and shaped to receive said upper portion snugly but sufficiently loose to allow swivel of said head relative to said shank prior to said set screw being urged against said upper portion.

7. The screw according to claim 5 wherein:

a) said upper portion is threaded coaxially with respect to said shank axis of rotation.

8. The screw according to claim 7 wherein:

a) said upper portion threaded portion is threaded on a spherical surface in such a manner that only a single central turn of the thread is complete, so as to allow capture of said shank upper portion in said chamber after passage of said upper portion through said head first bore.

9. The screw according to claim 1 wherein:

a) said shank includes a polyhedrally surfaced upper bore coaxially aligned with said axis; said upper bore being sized and shaped to receive an installation tool and receive torque therefrom.

10. The screw according to claim 1 wherein:

a) said head includes a third bore on an opposite side relative to said second bore and intersecting with said chamber; and further including:

b) a second set screw received in said third bore for operably locking against said shank upper potion.

11. The set screw according to claim 10 wherein:

a) said second and third bores are aligned to non radially intersect said chamber.

12. The set screw according to claim 11 wherein:

a) said first and second set screws engage said shank upper portion generally tangentially.

13. The screw according to claim 10 wherein:

a) said set screws each have respective drive heads that break away at a preselected toque.

14. The screw according to claim 10 wherein:

a) said set screws each abuts against said shank upper portion second thread during tightening of said set screws so as to lock said shank upper portion relative to said head.

15. The screw according to claim 10 wherein:

a) each of said set screws include a deformable forward point that abuts against said shank upper portion upon advancement and deforms both to lock said shank in position relative to said head and to reduce the likelihood of said set screws being inadvertently removed from respective bores thereof.

16. A swivel head bone screw having a shank and a head wherein:

a) said shank has an upper ball;

b) said head has an internal chamber for receiving said ball through a bore in said head in a ball and socket arrangement; and wherein c) said screw includes a locking mechanism to lock said ball in a fixed position relative to said head d) said bore and said ball include mating threads whereby said ball is screwed through said bore and then released to swivel in said chamber.

17. The bone screw according to claim 16 wherein:

a) said locking mechanism includes a set screw mounted in said head and positioned to engage said ball when said ball is in said chamber.

\* \* \* \* \*